US005836924A

United States Patent [19]

Kelliher et al.

[11] Patent Number: 5,836,924

[45] Date of Patent: Nov. 17, 1998

[54] FEEDING TUBE APPARATUS WITH ROTATIONAL ON/OFF VALVE

[75] Inventors: John Kelliher, Tucson; Thomas Dew, Oro Valley; Arturo Fern, Tuscon; Hoang Chi Le, Tucson; Charles Theurer, Tucson, all of Ariz.

[73] Assignee: MRI Manufacturing and Research, Inc., Tucson, Ariz.

[21] Appl. No.: 775,869

[22] Filed: Jan. 2, 1997

[51] Int. Cl.[6] ........ A61M 5/00

[52] U.S. Cl. ........ 604/248; 604/96; 604/104; 604/246

[58] Field of Search ........ 604/96, 104, 105, 604/174, 175, 245, 246, 247, 248, 256, 280, 264

[56] References Cited

U.S. PATENT DOCUMENTS

| | | |
|---|---|---|
| 3,331,371 | 7/1967 | Rocchi et al. . |
| 3,467,082 | 9/1969 | Gilbert . |
| 3,794,032 | 2/1974 | Derouineau . |
| 4,344,435 | 8/1982 | Aubin . |
| 4,369,789 | 1/1983 | LeVeen et al. . |
| 4,390,017 | 6/1983 | Harrison et al. . |
| 4,687,470 | 8/1987 | Okada . |
| 4,781,704 | 11/1988 | Potter . |
| 5,078,701 | 1/1992 | Grassi et al. . |
| 5,152,756 | 10/1992 | Quinn et al. . |
| 5,419,764 | 5/1995 | Roll . |
| 5,527,280 | 6/1996 | Goelz . |
| 5,549,657 | 8/1996 | Stern et al. . |
| 5,556,385 | 9/1996 | Andersen . |

*Primary Examiner*—Ronald Stright, Jr.
*Assistant Examiner*—Bhisma Mehta
*Attorney, Agent, or Firm*—Thomas I. Rozsa; Tony D. Chen

[57] ABSTRACT

A feeding apparatus has a user-activated rotatable feeding valve. The feeding apparatus is used in conjunction with a feeding connector which has a connecting end connected to the user-activated rotatable feeding valve, and which can be turned on or off by rotating the feeding connector.

9 Claims, 4 Drawing Sheets

FEEDING TUBE APPARATUS WITH ROTATIONAL ON/OFF VALVE

BACKGROUND OF THE INVENTION

1. Field of the Invention

The present invention generally relates to the field of medical devices. More particularly, the present invention relates to a feeding apparatus with a rotational on/off valve.

2. Description of the Prior Art

In the art, feeding tubes are medical devices which carry liquid food (formula) into a patient's digestive tract. The feeding tube comprises a connector which is connected to the formula, a feeding channel and a method of retention which can be a balloon retention or a collapsible, preformed retention.

A low profile feeding tube is designed to minimize the external portion of the feeding tube so as to enhance an active patient's comfort and lifestyle. It is used primarily for active children who require feeding through an abdominal stoma into the stomach.

A known prior art valve is an anti-reflux valve which allows formula to flow to the patient, but prevents gastric contents from flowing from the patient (i.e. refluxing) through the feeding tube. The anti-reflux valve can be a duckbill valve or a flap valve, for example, the flap valve is comparable to the cap on top of some diesel engines' vertical exhaust pipes. The cap opens when the pressure of the exhaust is great enough, and closes when the pressure is too low.

The problem with both the duckbill and the flap valves in a feeding application is that the mechanisms which ensure complete closure may degrade to the point that the valve malfunctions before the use of the device is discontinued. First, feeding solution and gastric contents can accrue in the area where a seal is intended to be formed, thus disrupting the seal. Second, repeated opening of the valve weakens the mechanism used to close the valve.

The following eleven (11) prior art patents are found to be pertinent to field of the present invention:

1. U.S. Pat. No. 3,467,082 issued to Gilbert on Sep. 16, 1969 for "Dental Syringe For Oral Hygiene" (hereafter "the Gilbert Patent");

2. U.S. Pat. No. 3,331,371 issued to Rocchi et al. on Jul. 18, 1967 for "Catheter Having Internal Flow Valve At Distal End Thereof" (hereafter "the Rocchi Patent");

3. U.S. Pat. No. 3,794,032 issued to Derouineau on Feb. 26, 1974 for "Supporting Cuff For Transfusions" (hereafter "the Derouineau Patent");

4. U.S. Pat. No. 4,344,435 issued to Aubin on Aug. 17, 1982 for "Method And Surgically Implantable Apparatus For Providing Fluid Communication With The Interior Of The Body" (hereafter "the Aubin Patent");

5. U.S. Pat. No. 4,369,789 issued to LeVeen et al. on Jan. 25, 1983 for "Inflatable Gastric Feeding Tube" (hereafter "the LeVeen Patent");

6. U.S. Pat. No. 4,390,017 issued to Harrison et al. on Jun. 28, 1983 for "Enteral Feeding System" (hereafter "the Harrison Patent");

7. U.S. Pat. No. 4,687,470 issued to Okada on Aug. 18, 1987 for "Catheter For Nasogastric Intubation" (hereafter "the Okada Patent");

8. U.S. Pat. No. 4,781,704 issued to Potter on Nov. 1, 1988 for "Feeding Tube Assembly With Collapsible Connector" (hereafter "the Potter Patent");

9. U.S. Pat. No. 5,078,701 issued to Grassi et al. on Jan. 7, 1992 for "Wire Guided Intestinal Catheter" (hereafter "the Grassi Patent");

10. U.S. Pat. No. 5,152,756 issued to Quinn et al. on Oct. 6, 1992 for "Distal Gripping Tip For Enteral Feeding Tube" (hereafter "the Quinn Patent"); and 11. U.S. Pat. No. 5,419,764 issued to Roll on May 30, 1995 for "Percutaneous Twisting Lock Catheter" (hereafter "the Roll Patent").

The Gilbert Patent discloses a dental syringe for oral hygiene. It comprises a valve housing which is detachably secured to the dispensing end of a faucet, a valve utilized to control the flow through the valve housing, and a connection fitting releasably secured to the valve housing for coupling a syringe via a flexible hose.

The Rocchi Patent discloses a catheter having an internal flow valve at its distal end. It comprises a tube with a closed end, an open end, and a fluid entrance hole in the wall adjacent to the closed end. A valve is provided within the tube adjacent to the fluid entrance hole. The valve comprises a rubber ball which is slightly larger than the inner diameter of the tube. The ball is positioned within the tube so that it completely covers the fluid entrance hole. The valve is operable between a position in which the valve extends completely across and closes the fluid entrance hole to prevent fluid from entering the tube, and a position in which the fluid entrance hole is uncovered to permit fluid to enter the tube. A valve operating cord extends from the valve to the open end of the tube to permit the valve to be operated between its two positions.

The Derouineau Patent discloses a supporting cuff for transfusions or perfusions. It comprises a base structure adapted to be secured to a patient's limb and a valve removably fitted on the base structure. The valve has two inlet ports adapted to be connected to tubes originating from bottles containing transfusion fluids and one outlet port adapted to be connected to a catheter to be lodged in the patient's limb. Movement of a rotatable lever on the valve determines which of the bottles will be rendered operable.

The Aubin Patent discloses a method and surgically implantable apparatus for providing fluid communication with the interior of the body. It comprises an annular body permanently implanted in the abdominal wall of a patient and provides fluid communication to an internal tube placed in the gastrointestinal tract to facilitate feeding of the patient. The annular body houses a spring biased valve which is opened by coupling the annular body to an external conduit for nutrient fluid. The annular body includes flanges and tissue fixation material which permit regrowth of the abdominal wall tissue about the annular body.

The LeVeen Patent discloses an inflatable gastric feeding tube for instilling fluids into the stomach of a patient. The tube comprises thin flexible inner and outer cylindrical walls which are sealed together at their proximal and distal ends to form an inflatable structure.

The Harrison Patent discloses an enteral feeding system. It comprises reversal of the male-female connections on a standard enteral feeding system, and a safety pressure relief on the male adapter of the feeding tube assembly.

The Okada Patent discloses a catheter for nasogastric intubation. It comprises a catheter which is inserted and encased into a plastic sheath tube. The sheath tube has a longitudinal tear-off line over the full length. The sheath tube and the catheter can be inserted through the nostril and into the intestines and/or the stomach, and after insertion, the sheath tube is withdrawn by longitudinally tearing-off the sheath tube externally of the nostril. The sheath tube is removed such that only the catheter remains in position within the patient's stomach.

The Potter Patent discloses a feeding tube assembly with a collapsible outlet connector. It comprises a guide tip, a hollow tube, and an enlarged bolus located between the guide tip and the distal end of the hollow tube. The bolus defines an opening for the tube outlet minimizing occlusion or clogging of the opening. A Y-shaped connector is attached to the proximal end of the hollow tube by an adapter sleeve and provides for the administration of fluids into the tube assembly.

The Grassi Patent discloses a wire guided intestinal catheter. It comprises a tube with an upstream end and a downstream end. The tube has three lumens: a first lumen for feeding, a second lumen for suction and a third lumen which vents the suction lumen. At the upstream end of the tube is a fitting for connecting the suction lumen to suction, a fitting for connecting the feeding lumen to a source of the nutritive or medical material and a structure for venting the vent lumen to atmosphere.

The Quinn Patent discloses a distal gripping tip for an enteral feeding tube. The enteral feeding tube comprises a distal end, a proximal end and an attachment that is adhered to the distal end. The attachment comprises a rigid stem portion which extends from the distal end and a spherical tip at one end of the rigid stem portion.

The Roll Patent discloses a percutaneous twisting lock catheter. It comprises a flexible tube, a catheter body, a reel, and a flexible tension member. The flexible tube is adapted to connect to a human body. The catheter body is coupled to the flexible tube and adapted for coupling to a reservoir tube. The reel is rotatable about a longitudinal centerline, where the flexible tension member is wound around when the catheter body is tightened. The reel has a hole adapted to convey the fluid therethrough in a direction parallel to the longitudinal centerline. The flexible tension member extends through the flexible tube and is wrapped around the reel.

It is desirable to have a very efficient and also very effective design and construction of a feeding apparatus which has a rotatable feeding valve, thereby eliminating the problems of prior art valves.

SUMMARY OF THE INVENTION

The present invention is a feeding apparatus which has a user-activated rotatable feeding valve. The feeding apparatus is used in conjunction with a standard feeding connector which is conventional in the art. The feeding connector has a connecting end which is connected to the user-activated feeding valve, which can be turned on or off by twisting the feeding connector.

The present invention avoids the problems in the prior art which cause valve function degradation. First, there is no possibility for any foreign material to accrue in the seal area, since each time the valve is closed, the mechanism effectively wipes the seal area clean. Secondly, there is no internal mechanism used to close the valve which can weaken. In the present invention, the mechanism is an externally applied force which is a person's fingers rotating the valve. Additionally, the present invention offers an advantage when decompression of the digestive tract is performed. In the prior art valves, the method of decompression was accomplished by inserting a hollow tube through the valve, which required an additional device whose only purpose is to decompress. In the present invention, decompression is accomplished with the standard connecting tubes which are used during feeding.

It is therefore an object of the present invention to provide a feeding apparatus which comprises a user-activated rotatable feeding valve and used in conjunction with a feeding connector. The feeding connector is connected to the user-activated feeding valve, which can be rotated on or off by twisting the feeding connector, where the feeding apparatus avoids the cause of valve function degradation.

It is also an object of the present invention to provide a feeding apparatus which comprises a user-activated rotatable feeding valve, where there is no possibility for any foreign material to accrue in the seal area, since each time the feeding valve is closed, the user-activated rotatable feeding valve effectively wipes the seal area clean.

It is an additional object of the present invention to provide a feeding apparatus which comprises a user-activated rotatable feeding valve, so that there is no internal mechanism used to close the feeding valve which can weaken. The user-activated rotatable feeding valve uses an externally applied force which is a person's fingers rotating the valve.

It is a further object of the present invention to provide a feeding apparatus which comprises a user-activated rotatable feeding valve, where decompression can be accomplished with standard connecting tubes which are used during feeding.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
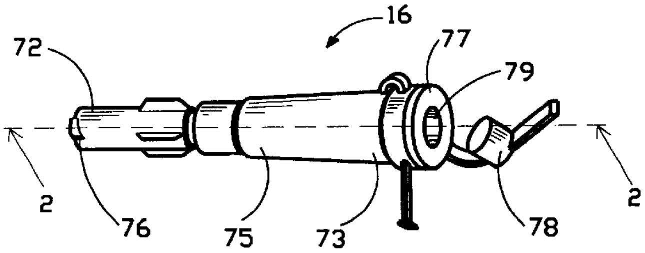
FIG.1 (PRIOR ART)
FIG. 1 is a perspective view of a prior art feeding connector which is used in conjunction with the present invention feeding apparatus.
Figure 2:
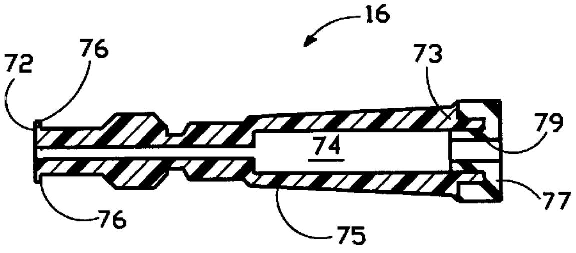
FIG.2 (PRIOR ART)
FIG. 2 is a cross-sectional view taken along line 2—2 of FIG. 1.

Referring to FIGS. 1 and 2, there are shown respective perspective and cross-sectional views of a prior art feeding connector 16 used in conjunction with the present invention feeding apparatus 110. The feeding connector 16 has a distal connecting end 72, a proximal end 73, a central interior passageway 74 which extends between the distal connecting end 72 and the proximal end 73, and an exterior sidewall 75. The exterior sidewall 75 has two opposite retaining ears 76 located adjacent to the distal connecting end 72, where the retaining ears 76 secure the distal connecting end 72 to the coupling member 154. A cap 77 is provided with the feeding connector 16 and is attached at the proximal end 73 of the feeding connector 16. A secure safety plug 78 is also provided with the feeding connector 16 and it is used for plugging the opening 79 on the cap 77 when not in use. A tubing/adapter system (not shown) is used for connecting to the feeding connector 16 for bolus and continuous feeding.

Figure 3:
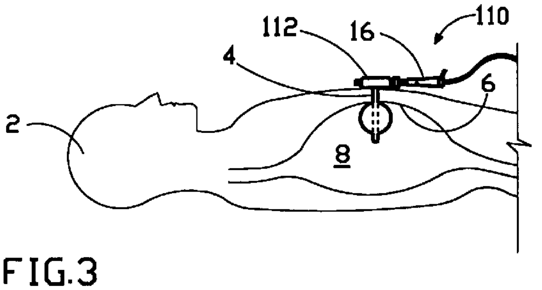
FIG. 3 is an illustration of the present invention feeding apparatus inserted through the abdominal wall of an individual and terminated in the stomach.

Referring to FIG. 3, there is depicted the present invention feeding apparatus 110 used by an individual 2 for long-term enteral feeding. The feeding apparatus 110 is installed by insertion through a surgical opening 4 at the abdominal wall 6 of the individual 2 and terminating in the stomach 8. The feeding apparatus 110 comprises a low profile feeding tube 112 and a rotatable valve assembly 114.

Figure 4:
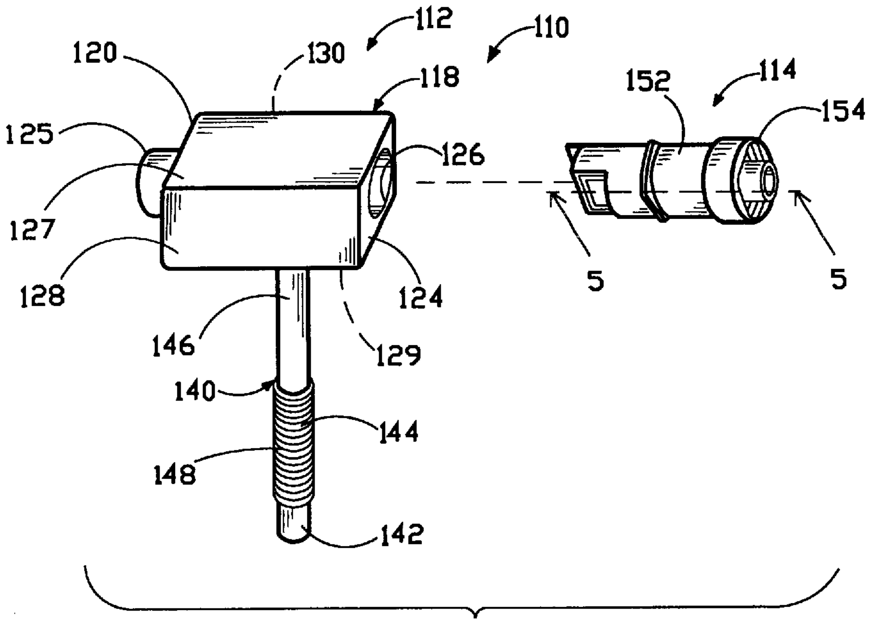
FIG. 4 is an exploded perspective view of the low profile feeding tube and the rotatable valve assembly, showing the preferred embodiment of the present invention feeding apparatus.

Referring to FIG. 4, there is shown an exploded perspective view of the low profile feeding tube 112 and the rotatable valve assembly 114 of the present invention feeding apparatus 110. The low profile feeding tube 112 has a generally T-shaped body which has an external main retention portion 118 and a transverse flexible hollow tube or shaft portion 140 with an internal retention balloon 148. The external retention portion 118 has a proximal end 124 with a socket opening 126, a distal end 120 with an inlet port 125, and four adjacent sidewalls 127, 128, 129 and 130. The inlet port 125 has an aperture 122 thereto (see FIG. 5).

It will be appreciated that the low profile feeding tube 112 depicted is only one illustration of a catheter. It is also within the spirit and scope of the present invention to utilize other types of low profile gastrostomy feeding devices.

Figure 5:
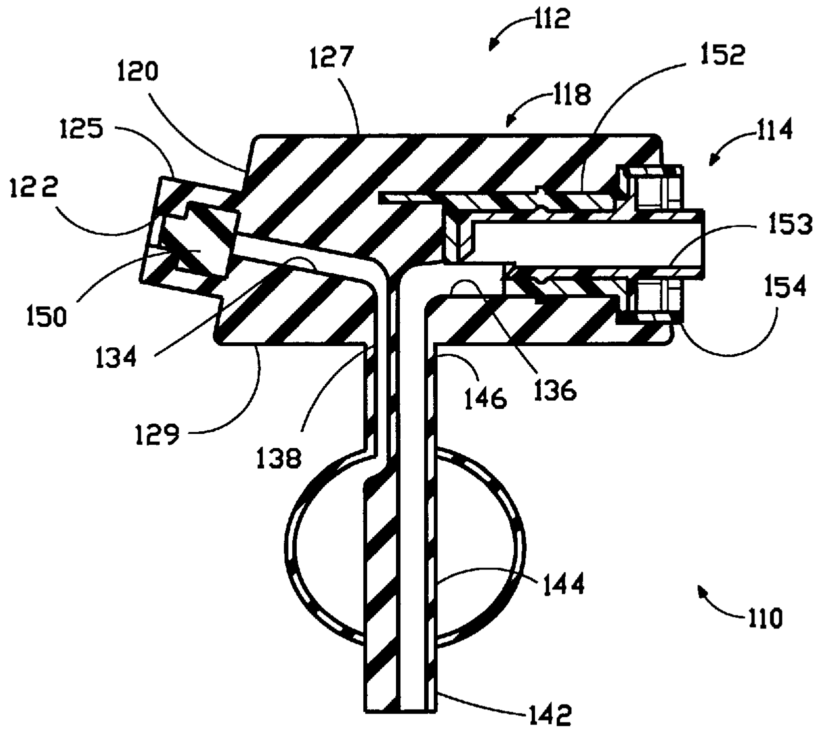
FIG. 5 is an enlarged cross-sectional view of the rotatable valve assembly installed in the low profile feeding tube of the present invention feeding apparatus shown in FIG. 4, showing the internal retention balloon in its inflated condition and the rotatable valve assembly in its open condition.

FIG. 5 shows an enlarged cross-sectional view of the feeding apparatus 110, showing the rotatable valve assembly 114 installed in the external retention portion 118 of the low profile feeding tube 112. Referring to FIGS. 4 and 5, the external retention portion 118 of the low profile feeding tube 112 is provided with an interior channel 134 and an opposite interior channel 136. The interior channel 134 communicates with the aperture 122 of the inlet port 125 and extends from the inlet port 125 to the internal retention balloon 148 of the low profile feeding tube 112. The interior channel 136 communicates with the socket opening 126 at the proximal end 124 of the external retention portion 118 of the low profile feeding tube 112 and extends from the proximal end 124 of the external retention portion 118 to the flexible shaft portion 140 of the low profile feeding tube 112. The interior channel 136 will provide nutritional support to enter into the body of the individual. The interior channel 134 will provide a means to inflate and deflate the internal retention balloon 148.

The flexible hollow shaft portion 140 has a distal portion 144 with a distal end opening 142 and a proximal end 146. The proximal end 146 of the tube portion 140 is located adjacent to the bottom sidewall 129 of the external retention portion 118 of the low profile feeding tube 112. The internal retention balloon 148 is integrally formed on the distal portion 144 of the flexible shaft portion 140 or may be secured by any suitable means known to one skilled in the art. The internal retention balloon 148 is inflated within the stomach of the individual such that the internal retention balloon 148 retains the hollow flexible shaft portion 140 within the stomach of the individual (see FIG. 3). The interior channel 134 of the feeding apparatus 110 permits the retention balloon 148 to be inflated after the flexible shaft portion 140 is inserted thereto. Once the retention balloon 148 is inflated (see FIG. 5), the low profile feeding tube 112 is retained in its normal position. The internal retention balloon 148 is inflated traditionally by using a conventional syringe (not shown) at the aperture 122 of the inlet port 125 of the feeding apparatus 110. A flexible plug 150 is provided with the low profile feeding tube 112 for plugging-up the aperture 122.

It will be appreciated that the internal retention balloon 148 is only but one method of retaining the hollow flexible shaft portion 140 within the stomach of the individual. It is emphasized that while the internal retention balloon 148 is preferred, it is also within the spirit and scope of the present invention to have a collapsible, preformed retention which is standard in the art.

Figure 6:
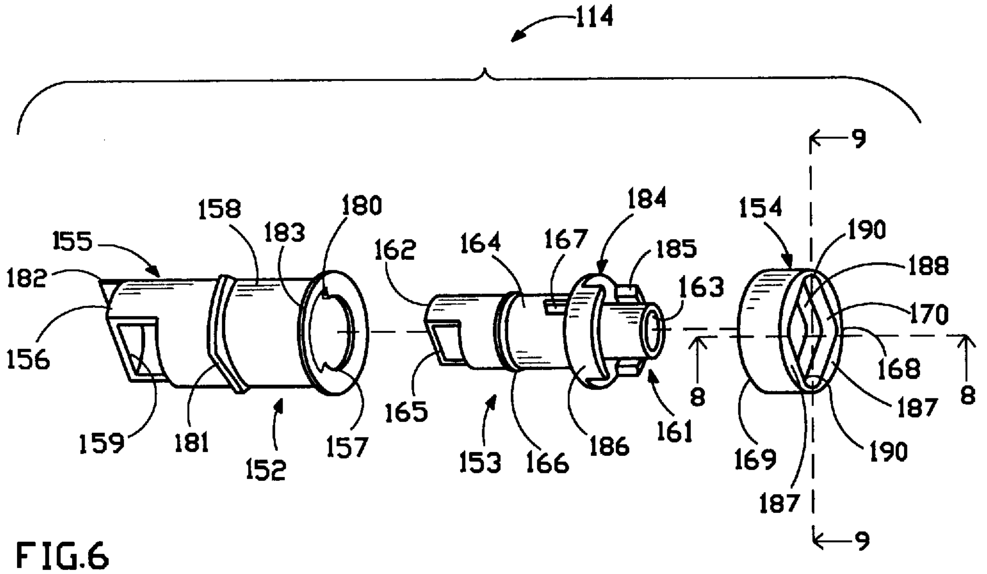
FIG. 6 is an exploded perspective view of the rotatable valve assembly of the present invention feeding apparatus shown in FIG. 4.
Figure 8:
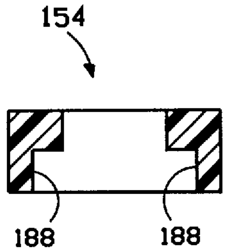
FIG. 8 is a cross-sectional view taken along line 8—8 of FIG. 6.
Figure 9:
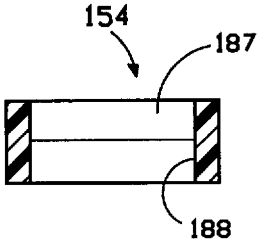
FIG. 9 is a cross-sectional view taken along line 9—9 of FIG. 6.
Figure 7:
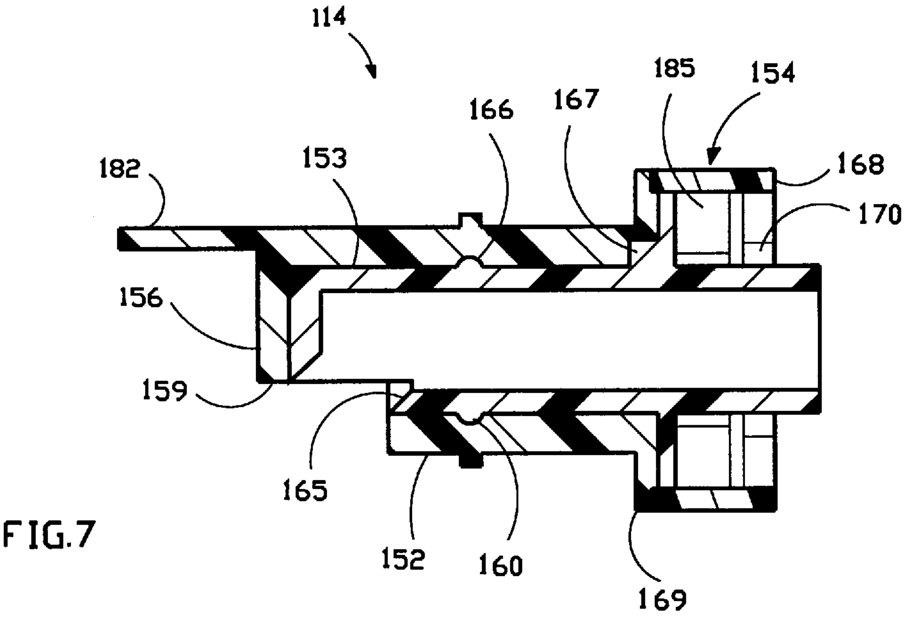
FIG. 7 is a longitudinal cross-sectional view of the rotatable valve assembly in its open condition shown in FIG. 4.

FIGS. 6 and 7 show respective exploded perspective view and cross-sectional view of the rotatable valve assembly 114 of the present invention feeding apparatus 110, where the rotatable valve assembly 114 is in its open or activate condition (see FIG. 7). Referring to FIGS. 5, 6 and 7, the rotatable valve assembly 114 comprises an outer shell member 152, an inner shell member 153 rotatably installed within the outer shell member 152 and a circular coupling member 154. The outer shell member 152 has a generally hollow cylindrical shaped body 155 which has a closed distal end 156, an open proximal end 157, a periphery rim 183 surrounding the open proximal end 157, and a circumferential sidewall 158. The sidewall 158 of the hollow cylindrical shaped body 155 has a side aperture 159 which is located adjacent to the closed distal end 156, an exterior protruding annular ridge or ledge 181 located adjacent to the middle of the body 155, and a recess 180 located on the interior of the periphery rim 183. The hollow cylindrical shaped body 155 of the outer shell member 152 further has an interior annular groove 160 which is located approximately the same location as the exterior protruding annular ridge 181 and a flange

182 which extends out from the closed distal end 156. The body 155 of the outer shell member 152 is press-fitted or installed in any other suitable means within the opening 126 at the proximal end 124 of the retention portion 118 of the low profile feeding tube 112, such that the exterior annular ridge 181 and the flange 182 prevents the outer shell member 152 from rotational and vertical movements.

The inner shell member 153 has a generally hollow cylindrical shaped body 161 which has a closed distal end 162, an open proximal rim 163, a disk-shaped member 184 located adjacent to the open proximal rim 163, and a circumferential sidewall 164. The circumferential sidewall 164 of the inner shell member 153 has a complementary side aperture 165 which corresponds with the side aperture 159 of the outer shell member 152, an exterior protruding annular bulge or ridge 166 located approximately in the middle, and a protruding flange 167 below the disk-shaped member 184. There are provided two spaced apart opposite flanges 185 and 186 located on the periphery of the disk member 184.

The outer diameter of the inner shell member 153 is slightly smaller than the inner diameter of the proximal open end 157 of the outer shell member 152, so that the inner shell member 153 is rotatably press-fitted within the outer shell member 152, where the exterior protruding annular ridge 166 snaps perfectly within the interior annular groove 160 (see FIG. 7) and the bottom of the disk-shaped member 184 abuts against the top of the periphery rim 183 of the outer shell member 152. Also the protruding flange 167 of the inner shell member 153 fits within the recess 180 provided on the outer shell member 152, so that the protruding flange 167 can move within this recess 180 to open or close the valve assembly 114.

Referring to FIGS. 5, 6, 7, 8, and 9, the coupling member 154 has a proximal rim 169, a distal rim 168, and an access opening 170 therethrough. Two opposite retaining flanges 187 are integrally formed with the interior periphery of the distal rim 168 of the coupling member 154 and extend downwardly to a middle of the coupling member 154, and thereby forms an interior annular slot or groove 188. The proximal rim 169 of the coupling member 154 is attached to the top of the periphery rim 183 of the outer shell member 152, such that the disk-shaped member 184 of the inner shell member 153 is movable within the coupling member 154, where the opposite flanges 185 and 186 of the inner shell member 153 are respectively rotated within the slot 188 provided on the coupling member 154. The coupling member 154 may be bonded or attached by any other suitable means known to one skilled in the art Referring to FIGS. 1 through 9, the feeding connector 16 is installed on the rotatable valve assembly 114 by inserting the distal connecting end 72 to the opening 170 of the coupling member 154 and aligning the two opposite retaining ears 76 with two gaps 190 provided on the distal rim 168 of the coupling member 154, and its two retaining ears 76 seat into the slot 188. Rotating the feeding connector 16 which in turn rotates the. inner shell member 153, locks the feeding connector 16 in place because the retaining ears 76 rotate behind the two opposite retaining flanges 187 on the coupling member 154. When the rotatable valve assembly 114 is in its open condition, the complementary side aperture 165 of the inner shell member 153 communicates with the side aperture 159 of the outer shell member 152 for allowing liquid food or etc. to flow therethrough. When the rotatable valve assembly 114 is in its closed condition, the complementary side aperture 165 of the inner shell member 153 will be located away from the side aperture 159 of the outer shell member 152 to prevent the liquid food or etc. to flow through the rotatable valve assembly 114.

The present invention feeding apparatus 110 conforms to conventional forms of manufacture or any other conventional way known to one skilled in the art. By way of example, the low profile feeding tube 112 may be made of rubber or rubber-like material and the valve assembly 114 may be made of plastic or rigid material. The manufacturing process which could accommodate the construction of the feeding apparatus 110 may be injection, thermoform, etc. or other molding process.

Figure 10:
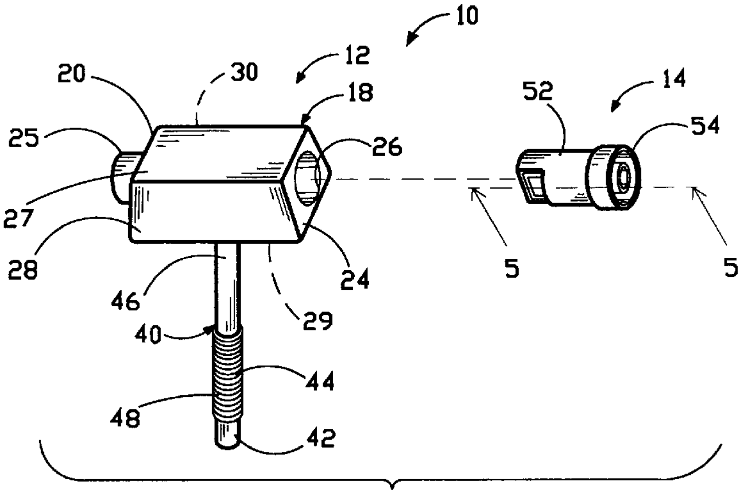
FIG. 10 is an exploded perspective view of the low profile feeding tube and the rotatable valve assembly, showing an alternative embodiment of the present invention feeding apparatus.

Referring to FIG. 10, there is shown an exploded perspective view of an alternative embodiment of the present invention feeding apparatus 110, showing the rotatable valve assembly 14 installed in the low profile feeding tube 12. The low profile feeding tube 12 has a generally T-shaped body which has an external main retention portion 18 and a transverse flexible hollow tube or shaft portion 40 with an internal retention balloon 48. The external retention portion 18 has a front end 24 with a socket opening 26, a rear end 20 with an inlet port 25, and four sidewalls 27, 28, 29 and 30. The inlet port 25 has an opening 22 thereto (see FIG. 11).

It will be appreciated that the low profile feeding tube 12 depicted is only one illustration of a catheter. It is also within the spirit and scope of the present invention to utilize other types of low profile gastrostomy feeding devices.

Figure 11:
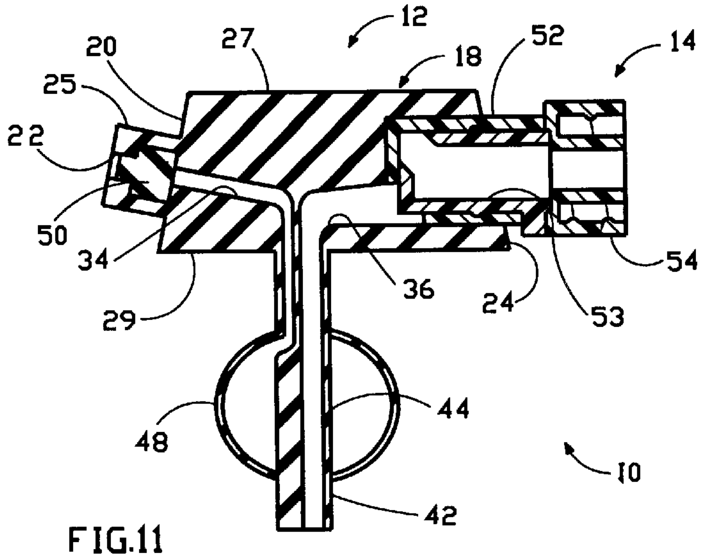
FIG. 11 is an enlarged cross-sectional view of the rotatable valve assembly installed in the low profile feeding tube of the present invention feeding apparatus shown in FIG. 10, showing the internal retention balloon in its inflated condition and the rotatable valve assembly in its closed condition.

Referring to FIG. 11, there is shown an enlarged cross-sectional view of the rotatable valve assembly 14 installed in the external retention portion 18 of the low profile feeding tube 12. The external retention portion 18 of the low profile feeding tube 12 is provided with an interior channel 34 and an opposite interior channel 36. The interior channel 34 communicates with the opening 22 of the inlet port 25 and extends from the inlet port 25 to the internal retention balloon 48 of the low profile feeding tube 12. The interior channel 36 communicates with the socket opening 26 at the front end 24 of the external retention portion 18 of the low profile feeding tube 12 and extends from the front end 24 of the external retention portion 18 to the flexible shaft portion 40 of the low profile feeding tube 12. The interior channel 36 will provide nutritional support to enter into the body of the individual. The interior channel 34 will provide a means to inflate and deflate the internal retention balloon 48.

Referring to FIG. 10, the transverse flexible hollow shaft portion 40 has a distal portion 44 with a distal end opening 42 and a proximal end 46. The proximal end 46 of the tube 40 is located adjacent to the sidewall 29 of the external retention portion 18 of the low profile feeding tube 12. The internal retention balloon 48 is integrally formed on the distal portion 44 of the flexible shaft portion 40 or may be secured by any suitable means known to one skilled in the art. The internal retention balloon 48 is inflated within the stomach of the individual such that the internal retention balloon 48 retains the hollow flexible shaft portion 40 within the stomach of the individual (see FIG. 3). The interior channel 34 of the feeding apparatus 10 permits the retention balloon 48 to be inflated after the flexible shaft portion 40 is inserted. Once the retention balloon 48 is inflated (see FIG. 11), the low profile feeding tube 12 is retained in its normal position. The internal retention balloon 48 is inflated traditionally by using a conventional syringe (not shown) at the opening 22 of the inlet port 25 of the feeding apparatus 10. A flexible plug 50 is provided with the low profile feeding tube 12 for plugging-up the opening 22.

It will be appreciated that the internal retention balloon 48 is only but one method of retaining the hollow flexible shaft portion 40 within the stomach of the individual. It is emphasized that while the internal retention balloon 48 is preferred, it is also within the spirit and scope of the present invention to have a collapsible, preformed retention which is standard in the art.

Figure 12:
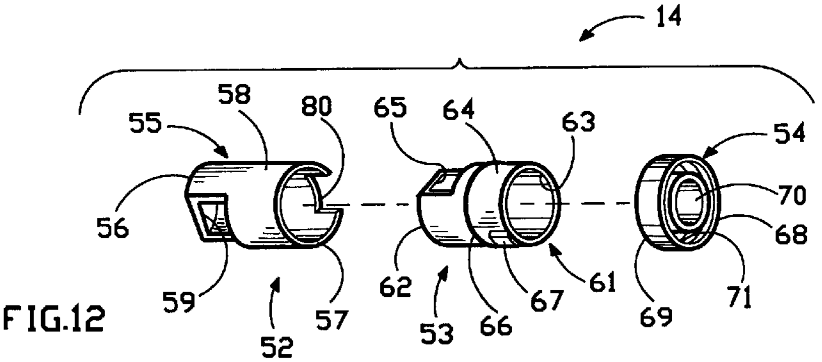
FIG. 12 is an exploded perspective view of the rotatable valve assembly of the present invention feeding apparatus shown in FIG. 10.
Figure 13:
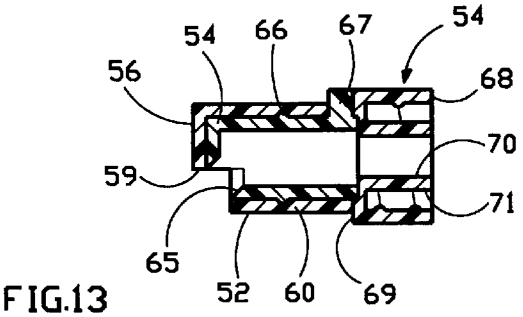
FIG. 13 is a longitudinal cross-sectional view of the rotatable valve assembly in its open condition shown in FIG. 10.

FIGS. 12 and 13 show respective exploded perspective view and cross-sectional view of the rotatable valve assembly 14 of the present invention feeding apparatus 10, where the rotatable valve assembly 14 is in its open or activate condition (see FIG. 13) and the rotatable valve assembly 14 is in its closed or deactivated condition (see FIG. 11). Referring to FIGS. 12 and 13, the rotatable valve assembly 14 comprises an outer shell member 52, an inner shell member 53 rotatably installed within the outer shell member 52 and a coupling member 54. The outer shell member 52 has a generally hollow cylindrical shaped body 55 which has a closed distal end 56, an open proximal end 57, and a circumferential sidewall 58. The sidewall 58 of the hollow cylindrical shaped body 55 has a side aperture 59 which is located adjacent to the closed distal end 56 and a side notch groove 80 which is located adjacent to the open proximal end 57 and opposite the side aperture 59. The hollow cylindrical shaped body 55 of the outer shell member 52 further has an interior annular groove 60 which is located approximately in the middle of the hollow cylindrical shaped body 55.

The inner shell member 53 has a generally hollow cylindrical shaped body 61 which has a closed distal end 62, an open proximal end 63, and a circumferential sidewall 64. The circumferential sidewall 64 of the inner shell member 53 has a complementary side aperture 65 which corresponds with the side aperture 59 of the outer shell member 52, an exterior protruding annular bulge or ridge 66 located approximately in the middle, and a protruding flange 67 located adjacent to the open proximal end 63.

The hollow cylindrical shaped body 61 of the inner shell 53 is smaller than the hollow cylindrical shaped body 55 of the outer shell member 52, so that the inner shell member 53 is rotatably press-fitted within the outer shell member 52, where the exterior protruding annular ridge 66 of the inner shell member 53 snaps perfectly within the interior annular groove 60 of the outer shell member 52. Also the protruding flange 67 of the inner shell member 53 fits within the side notch groove 80 of the outer shell member 52, so that the protruding flange 67 can move within this side notch groove 80 to an open condition (see FIG. 13) or a closed condition (see FIG. 11).

The coupling member 54 has a proximal end 68, a distal end 69 and a central bore 70 which extends from the proximal end 68 to the distal end 69. The proximal end 68 has an inlet port attachment 71 which corresponds to the conventional connection in the art, e.g., luer or luer-locking connection or any other suitable type of connection means. The distal end 69 of the coupling member 54 is attached to the open proximal end 63 of the inner shell member 53 such that the central bore 70 communicates with the open proximal end 63 of the inner shell member 53. The coupling member 54 may be bonded or attached by other suitable means known in the art.

Referring to FIGS. 10 through 13, once the feeding connector 16 is connected to the rotatable valve assembly 14, the feeding connector 16 is rotated in a clockwise or counter-clockwise direction, which in turn rotates the inner shell member 53 within the outer shell member 52 between the open position and the closed position. When the inner shell member 53 is in its open position, the complementary side aperture 65 communicates with the side aperture 59 of the outer shell member 52 for allowing liquid food or etc. to flow therethrough. When the inner shell member 53 is rotated in the opposite direction, the complementary side aperture 65 of the inner shell member 53 will be located away from the side aperture 59 of the outer shell member 52 (see FIG. 11) to prevent the liquid food or etc. to flow through the rotatable valve assembly 14.

Defined in detail, the present invention is a feeding apparatus for insertion through a surgical opening at the abdominal wall of an individual and terminates in the stomach, and used in conjunction with a feeding connector which has at least one lateral ear means, the apparatus comprising: (a) a generally T-shaped body having an external portion and a transverse flexible hollow shaft portion, the external portion having a proximal end with a socket opening, a distal end with an opening, and two opposite interior channels communicating with the openings at the proximal and distal ends respectively and the hollow shaft portion, the shaft portion having a distal section with a distal end opening and a proximal end; (b) an internal retention balloon integrally formed on the distal section of the hollow shaft portion of the T-shaped body such that the retention balloon is inflatable for retaining the shaft portion within the stomach of the individual; (c) a rotatable valve assembly including an outer shell member, an inner shell member rotatably installed within the outer shell member, and a circular coupling member; (d) the outer shell member having a generally hollow cylindrical shaped body, the cylindrical shaped body having a closed distal end, an open proximal end and a circumferential sidewall, the sidewall having a side aperture located adjacent to the distal end and a recess located adjacent to the proximal end and opposite the side aperture, the outer shell member installed within the socket opening at the proximal end of the external portion of the T-shaped body, where the side aperture on the sidewall of the outer shell member communicates with the interior channel at the proximal end of the external portion of the T-shaped body; (e) the inner shell member having a generally hollow cylindrical shaped body, the cylindrical shaped body having a closed distal end, an open proximal rim and a circumferential sidewall, the sidewall having a complementary side aperture located adjacent to the distal end and a protruding flange located adjacent to the proximal rim, the inner shell member rotatably installed within the outer shell member such that the protruding flange is retained within the recess on the sidewall of the outer shell member, where the inner shell member is rotatable between an open condition and a closed condition such that when the valve assembly is in its open condition, the complementary side aperture of the inner shell member communicates with the side aperture of the outer shell member for allowing liquid food to flow therethrough and when the valve assembly is in its closed condition, the complementary side aperture of the inner shell member is located away from the side aperture of the outer shell member to prevent liquid food from flowing therethrough; (f) a disk shaped member having a base portion with a central aperture, a hollow protruding attachment portion attached to the base portion and aligned with the aperture, and two opposite spaced apart retaining means attached to the base portion and encompassing the attachment portion, the base portion integrally attached to the proximal rim of the inner shell member; and (g) the circular coupling member having a proximal rim, a distal retaining means and an interior annular slot, the proximal rim attached to the proximal end of the outer shell member such that the coupling member encompasses the protruding attachment portion of the disk-shaped member and the two opposite spaced apart retaining means of the disk-shaped member; (h) whereby the feeding connector is connected to the hollow protruding attachment portion of the disk shaped member, the feeding connector rotated such that the at least one lateral ear means travels within the interior annular slot of the coupling member to engage the retaining means on the disk shaped member, which in turn rotates the inner shell member into the open condition to allow the liquid food to pass through the feeding apparatus, and when the feeding connector is rotated in the opposite direction, the at least one lateral ear means of the feeding connector engaged with the retaining means on the disk shaped member which in turn rotates the inner shell member back to the closed condition for preventing liquid food flow therethrough.

Defined broadly, the present invention is a feeding apparatus for insertion through an opening at the abdominal wall of an individual and terminates in the stomach, and used in conjunction with a feeding connector which has at least one lateral ear means, the apparatus comprising: (a) a structure having a main portion and a hollow shaft portion, the main portion having a proximal end with a socket opening, a distal end with an opening, and two interior channels communicating with the openings and the hollow shaft portion; (b) means for retaining the shaft portion of the structure within the stomach of the individual; (c) a valve assembly including an outer shell, an inner shell and a coupling member; (d) the outer shell having a distal end, a proximal end and a sidewall, the sidewall having an aperture located adjacent to the distal end and a recess located adjacent to the proximal end and opposite the aperture, the outer shell installed within the socket opening at the proximal end of the main portion of the structure, where the aperture on the sidewall of the outer shell communicates with one of the interior channels of the main portion of the structure; (e) the inner shell having a distal end, a proximal end and a sidewall, the sidewall having a complementary aperture located adjacent to the distal end and a protruding flange located adjacent to the proximal end, the inner shell installed within the outer shell such that the protruding flange is retained within the recess on the sidewall of the outer shell and the complementary aperture of the inner shell communicates with the aperture on the sidewall of the outer shell, where the protruding flange travels within the recess of the outer shell between an open condition and a closed condition so that when the valve assembly is in its open condition, the complementary aperture on the sidewall of the inner shell communicates with the aperture on the sidewall of the outer shell for allowing liquid food to flow therethrough, and when the valve assembly is in its closed condition, the complementary aperture of the inner shell is located away from the aperture of the outer shell to prevent liquid food from flowing therethrough; (f) a disk having a base, an attachment inlet port extending upwardly from the base, and at least one retaining means attached to the base, the base attached to the proximal end of the inner shell; and (g) the coupling member having a proximal rim, a distal retaining means and an interior groove, the proximal rim attached to the proximal end of the outer shell member such that the coupling member encompasses the attachment inlet port of the disk and the at least one retaining means of the disk; (h) whereby the feeding connector is connected to the attachment inlet port of the disk, the feeding connector rotated such that the at least one lateral ear means travels within the interior groove of the coupling member to engage the at least one retaining means on the disk, which in turn rotates the inner shell into the open condition to allow the liquid food to pass through the feeding apparatus, and when the feeding connector is rotated in the opposite direction, the at least one lateral ear means of the feeding connector engaged with the at least one retaining means on the disk which in turn rotates the inner shell back to the closed condition for preventing liquid food flow therethrough.

Defined more broadly, the present invention is a valve assembly used in conjunction with a low profile feeding tube and a feeding connector which has at least one lateral ear means, the valve assembly comprising: (a) an outer shell for installing into the low profile feeding tube and having a distal end, an open proximal end and a sidewall, the sidewall having an aperture located adjacent to the distal end; (b) an inner shell having a distal end, an open proximal end and a sidewall, the sidewall having a complementary aperture located adjacent to the distal end and a protruding flange located adjacent to the proximal end, the inner shell installed within the outer shell such that the complementary aperture of the inner shell communicates with the aperture of the outer shell, where the inner shell is turned between an open condition for allowing liquid food to flow therethrough and a closed condition for preventing liquid food from flowing therethrough; and (c) a coupling member having a distal end, a proximal end and a bore extending from the distal end to the proximal end, the distal end attached to the proximal end of the inner shell such that the bore communicates with the open proximal end of the inner shell; (d) whereby the valve assembly installable to the low profile feeding tube and the feeding connector is installable on the proximal end of the coupling member and turning the feeding connector which in turn turns the inner shell into the open condition for allowing the liquid food to pass through the valve assembly, and rotating the feeding connector in an opposite direction rotates the inner shell back to the closed condition for preventing the liquid food from flowing therethrough.

Defined even more broadly, the present invention is a valve assembly used in conjunction with a catheter, comprising: (a) an outer shell having a side aperture; (b) an inner shell installed within the outer shell and having a complementary side aperture, where the inner shell is turnable between an open position and a closed position such that when the valve assembly is in its open position, the complementary side aperture of the inner shell communicates with the side aperture of the outer shell for allowing liquid food to flow therethrough and when the valve assembly is in its closed position, the complementary side aperture of the inner shell is located away from the side aperture of the outer shell to block liquid food from flowing therethrough; and (c) a coupling member attached to the outer shell and having a bore communicating with the complementary side aperture of the inner shell which in turn communicates with the side aperture of the outer shell; (d) whereby turning the inner shell into the open position, the liquid food passes through the valve assembly, and turning the inner shell in an opposite direction back to the closed position, the liquid food is blocked.

Defined even further more broadly, the present invention is a valve assembly used in conjunction with a catheter, comprising: (a) an outer shell having an opening; (b) an inner shell installed within the outer shell and having an opening that corresponds with the opening of the outer shell; (c) means for coupling a feeding connector to the inner shell; and (d) means for allowing liquid to flow therethrough and also preventing the liquid food from flowing therethrough.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A feeding apparatus for insertion through an opening at the abdominal wall of an individual and terminating in the stomach, and used in conjunction with a feeding connector which has at least one lateral ear means, the apparatus comprising:

a. a structure having a main portion and a hollow shaft portion, the main portion having a proximal end with a socket opening, a distal end with an opening, and two interior channels communicating with the openings and the hollow shaft portion;

b. means for retaining said shaft portion of said structure within the stomach of the individual;

c. a valve assembly including an outer shell, an inner shell and a coupling member;

d. said outer shell having a distal end, of the outer shell a proximal end and a sidewall, the sidewall having an aperture located adjacent to the distal end of the outer shell and a recess located adjacent to the proximal end, said outer shell installed within said socket opening at said proximal end of said main portion of said structure, where the aperture on the sidewall of said outer shell communicates with one of said interior channels of said main portion of said structure;

e. said inner shell having a distal end, a proximal end and a sidewall, the sidewall having a complementary aperture located adjacent to the distal end of the inner shell and a protruding flange located adjacent to the proximal end, of the inner shell said inner shell installed within said outer shell such that the protruding flange is retained within said recess on said sidewall of said outer shell and the complementary aperture of said inner shell communicates with said aperture on said sidewall of said outer shell, where the protruding flange travels within said recess of said outer shell between an open condition and a closed condition so that when said valve assembly is in its open condition, the complementary aperture on said sidewall of said inner shell communicates with said aperture on said sidewall of said outer shell for allowing liquid food to flow therethrough, and when said valve assembly is in its closed condition, the complementary aperture of said inner shell is located away from said aperture of said outer shell to prevent liquid food from flowing therethrough;

f. a disk having a base, an attachment inlet port extending upwardly from the base, and at least one retaining means attached to the base, the base attached to said proximal end of said inner shell; and g. said coupling member having a proximal rim, a distal retaining means and an interior groove, the proximal rim attached to said proximal end of said outer shell member such that said coupling member encompasses said attachment inlet port of said disk and said at least one retaining means of said disk;

h. whereby the feeding connector is connected to said attachment inlet port of said disk, the feeding connector rotated such that the at least one lateral ear means travels within said interior groove of said coupling member to engage said at least one retaining means on said disk, which in turn rotates said inner shell into said open condition to allow the liquid food to pass through said feeding apparatus, and when the feeding connector is rotated in the opposite direction, the at least one lateral ear means of the feeding connector is engaged with said at least one retaining means on said disk which in turn rotates said inner shell back to said closed condition for preventing liquid food flow therethrough.

2. The feeding apparatus in accordance with claim 1 wherein said means for retaining said shaft portion within the stomach of the individual includes a retention balloon integrally formed on said shaft portion, where the retention balloon is inflatable.

3. The feeding apparatus in accordance with claim 2 wherein said retention balloon is inflated by using a syringe at said opening of said distal end of said main portion.

4. The feeding apparatus in accordance with claim 1 wherein said valve assembly is made of rigid material.

5. The feeding apparatus in accordance with claim 1 wherein said structure is made of rubber material.

6. A feeding apparatus for insertion through a surgical opening at the abdominal wall of an individual and terminating in the stomach, and used in conjunction with a feeding connector which has at least one lateral ear means, the apparatus comprising:

a. a generally T-shaped body having an external portion and a transverse flexible hollow shaft portion, the external portion having a proximal end with a socket opening, a distal end with an opening, and two opposite interior channels communicating with the openings at the proximal and distal ends respectively and the hollow shaft portion, the shaft portion having a distal section with a distal end opening and a proximal end;

b. an internal retention balloon integrally formed on said distal section of said hollow shaft portion of said T-shaped body such that the retention balloon is inflatable for retaining said shaft portion within the stomach of the individual;

c. a rotatable valve assembly including an outer shell member, an inner shell member rotatably installed within the outer shell member, and a circular coupling member;

d. said outer shell member having a generally hollow cylindrical shaped body, the cylindrical shaped body having a closed distal end, an open proximal end and a circumferential sidewall, the sidewall having a side aperture located adjacent to the distal end of the cylindrical shaped body and a recess located adjacent to the proximal end of the cylindrical shaped body and opposite the side aperture, said outer shell member installed within said socket opening at said proximal end of said external portion of said T-shaped body, where the side aperture on the sidewall of said outer shell member communicates with said interior channel at said proximal end of said external portion of said T-shaped body;

e. said inner shell member having a generally hollow cylindrical shaped body, the cylindrical shaped body having a closed distal end, an open proximal rim and a circumferential sidewall, the sidewall having a complementary side aperture located adjacent to the distal end of the cylindrical shaped body of the inner shell member and a protruding flange located adjacent to the proximal rim, said inner shell member rotatably installed within said outer shell member such that the protruding flange is retained within said recess on said sidewall of said outer shell member, where said inner shell member is rotatable between an open condition and a closed condition such that when said valve assembly is in its open condition, the complementary side aperture of said inner shell member communicates with said side aperture of said outer shell member for allowing liquid food to flow therethrough and when said valve assembly is in its closed condition, the complementary side aperture of said inner shell member is located away from said side aperture of said outer shell member to prevent liquid food from flowing therethrough;

f. a disk shaped member having a base portion with a central aperture, a hollow protruding attachment portion attached to the base portion and aligned with the aperture, and at least one retaining means attached to the base portion and encompassing the attachment portion, the base portion integrally attached to said proximal rim of said inner shell member; and g. said circular coupling member having a proximal rim, a distal retaining means and an interior annular slot, the proximal rim of the circular coupling member attached to said proximal end of said outer shell member such that said coupling member encompasses said protruding attachment portion of said disk shaped member and said at least one retaining means of said disk shaped member;

h. whereby the feeding connector is connected to said hollow protruding attachment portion of said disk shaped member, the feeding connector rotated such that the at least one lateral ear means travels within said interior annular slot of said coupling member to engage said at least one retaining means on said disk shaped member, which in turn rotates said inner shell member into said open condition to allow the liquid food to pass through said feeding apparatus, and when the feeding connector is rotated in the opposite direction, the at least one lateral ear means of the feeding connector is engaged with said at least one retaining means on said disk shaped member which in turn rotates said inner shell member back to said closed condition for preventing liquid food flow therethrough.

7. The feeding apparatus in accordance with claim 6 wherein said internal retention balloon is inflated by using a syringe at said inlet opening of said distal end of said external portion of said T-shaped body.

8. The feeding apparatus in accordance with claim 6 wherein said rotatable valve assembly is made of rigid material.

9. The feeding apparatus in accordance with claim 6 wherein said T-shaped body is made of rubber material.

* * * * *